(12) United States Patent
Sun et al.

(10) Patent No.: US 8,840,634 B2
(45) Date of Patent: Sep. 23, 2014

(54) DEVICE FOR PERFORMING AN INCISION

(75) Inventors: Jian Ping Sun, Singapore (SG); Tiow Hee Edmond Tan, Singapore (SG); Hue Chin Ling, Singapore (SG)

(73) Assignee: Medipurpose Pte Ltd, Singapore (SG)

( * ) Notice: Subject to any disclaimer, the term of this patent is extended or adjusted under 35 U.S.C. 154(b) by 251 days.

(21) Appl. No.: 13/056,681

(22) PCT Filed: Jul. 30, 2009

(86) PCT No.: PCT/SG2009/000269
§ 371 (c)(1),
(2), (4) Date: Jun. 6, 2011

(87) PCT Pub. No.: WO2010/014044
PCT Pub. Date: Feb. 4, 2010

(65) Prior Publication Data
US 2011/0264131 A1    Oct. 27, 2011

(30) Foreign Application Priority Data
Jul. 30, 2008  (SG) .............................. 200805669-9

(51) Int. Cl.
*A61B 17/32*    (2006.01)
*A61B 5/151*    (2006.01)
*A61B 5/15*    (2006.01)
*A61B 17/3209*    (2006.01)

(52) U.S. Cl.
CPC ............. *A61B 5/151* (2013.01); *A61B 5/15142* (2013.01); *A61B 5/1411* (2013.01); *A61B 17/32093* (2013.01)
USPC .......................................................... 606/182

(58) Field of Classification Search
CPC .. A61B 5/1411; A61B 5/151; A61B 5/15113; A61B 5/15117; A61B 5/15128; A61B 5/15194; A61B 5/15142; A61B 5/150022; A61B 5/15115
USPC ........ 606/181–183; 600/583; 42/70.06, 70.07
See application file for complete search history.

(56) References Cited

U.S. PATENT DOCUMENTS 2,590,516 A * 3/1952  De Von Breymann ....... 42/70.06
4,628,929 A * 12/1986 Intengan et al. .............. 606/182

(Continued)

FOREIGN PATENT DOCUMENTS

| | | |
|---|---|---|
| CA | 2728237 | 2/2010 |
| CN | 102112052 | 6/2011 |

(Continued)

OTHER PUBLICATIONS

Search Report for related European Patent Application No. EP09803220.4 dated Aug. 3, 2011.

(Continued)

*Primary Examiner* — Kathleen Holwerda
(74) *Attorney, Agent, or Firm* — Troutman Sanders LLP; Ryan A. Schneider; Benjamin C. Wiles

(57) ABSTRACT

A medical cutting device is disclosed in which a pivoted element (50) is actuated by a trigger (34) and a cutting blade (30) is attached to the pivoted element (50) by a flexible connector and cam elements (46, 49) cause the blade (30) to move in an essentially parabolic path when making an incision on a patient.

17 Claims, 22 Drawing Sheets

(56) References Cited

U.S. PATENT DOCUMENTS

| | | | |
|---|---|---|---|
| 5,397,334 A | * | 3/1995 | Schenk et al. ............... 606/182 |
| 5,772,677 A | * | 6/1998 | Mawhirt et al. ............... 606/181 |
| 6,042,595 A | * | 3/2000 | Morita ............................ 606/181 |
| 2003/0191415 A1 | | 10/2003 | Moerman et al. |

FOREIGN PATENT DOCUMENTS

| | | |
|---|---|---|
| EP | 1570792 | 9/2005 |
| EP | 1767149 A1 | 3/2007 |
| JP | 2008-535581 A | 4/2008 |
| JP | 2011529376 | 12/2011 |
| KR | 20110065443 | 6/2011 |
| MX | 2011001086 | 3/2011 |
| WO | 2005/102166 A1 | 3/2005 |
| WO | 2006/110572 A2 | 10/2006 |
| WO | 2008066491 | 6/2008 |
| WO | 2010014044 | 2/2010 |

OTHER PUBLICATIONS

International Preliminary Report on Patentability dated Sep. 23, 2010 for PCT Patent Application No. PCT/SG2009/000269.

Examination Report for related European Patent Application No. 09803220.4 dated Apr. 27, 2012.

Decision to Grant issued by the European Patent Office dated Mar. 1, 2013 for EP Application No. 09803220.4.

Examination Report for related European Patent Application No. EP09803220.4 dated Nov. 5, 2012.

Office Action dated Dec. 10, 2013 for Japanese Patent Application No. 2011-521065.

\* cited by examiner

DEVICE FOR PERFORMING AN INCISION

CROSS-REFERENCE TO RELATED APPLICATIONS

This application is a US National Stage of International Application No. PCT/SG2009/000269, filed 30 Jul. 2009, which claims the benefit of SG 200805669-9, filed 30 Jul. 2008.

FIELD

This invention relates to medical instruments, and more particularly to a lancet used for making incisions in patients.

BACKGROUND

Lancets are relatively small, hand-held medical cutting devices used for making incisions in patients such as, for example, in making incisions in the heels of infants to take blood samples. Hence, they are sometimes referred to as "heel sticks". A number of prior art lancets have been proposed including for example U.S. Pat. Nos. 5,314,441; 5,951,582; 6,402,595 and 6,221,089 to list a few. However, all of the prior lancets have suffered from one or more problems such as, for example, producing non-ideally shaped incisions, causing more pain than desired, and being subject to variations in the incisions depending upon use by different medical personnel. In addition, they have been quite costly to produce, which is a serious problem since they are used only once and then disposed.

The object of the present invention is to eliminate, or substantially reduce, these and other problems of prior art lancets.

SUMMARY

A medical cutting device including a pivoted element, a trigger and a cutting blade flexibly connected to the pivoted element for producing cutting movement of the blade in a substantially parabolic path.

DETAILED DESCRIPTION

Figure 1:
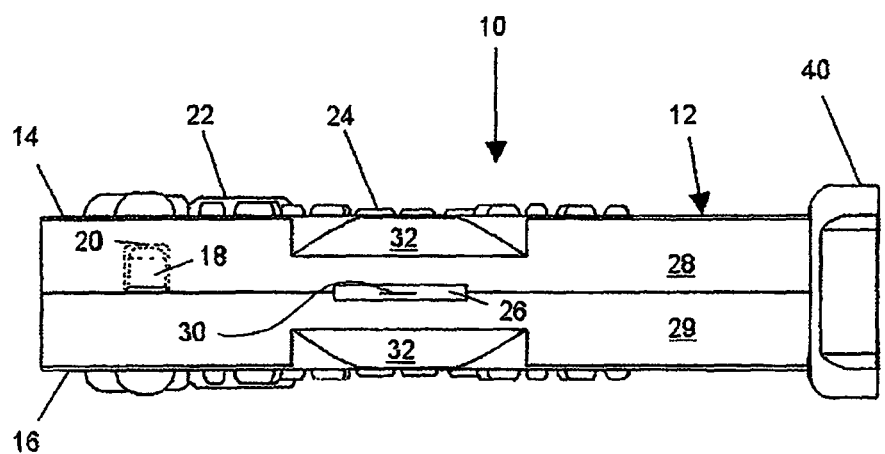
FIG. 1 is an elevational view of the bottom edge of the lancet.
Figure 2:
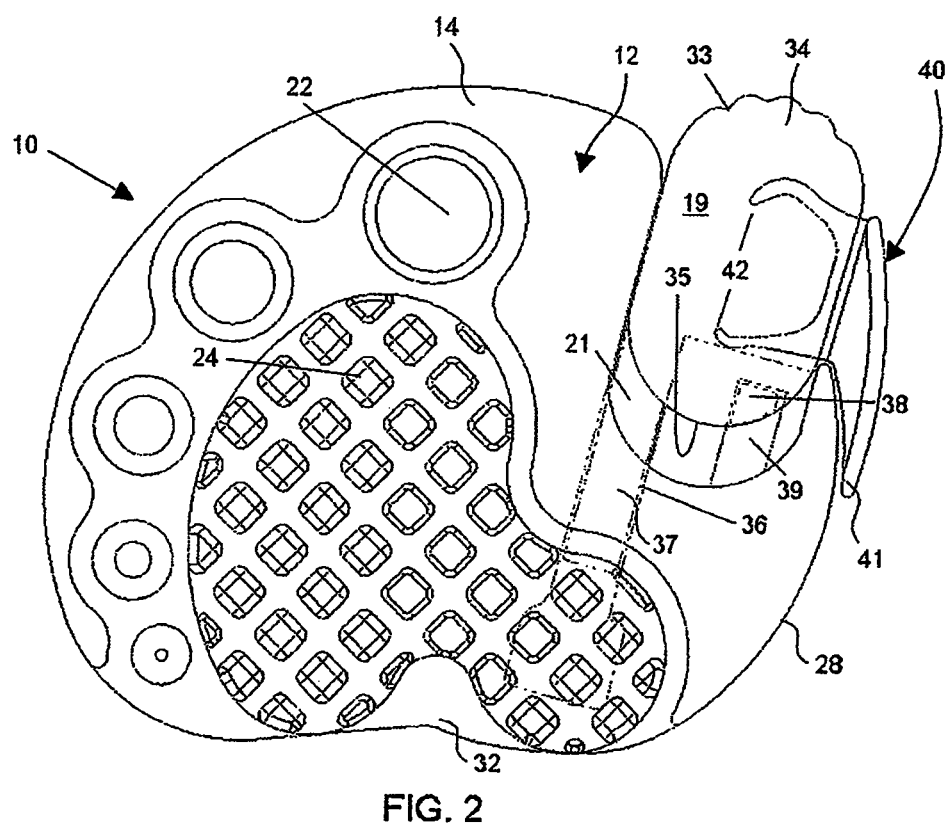
FIG. 2 is a top plan view of the lancet.

Referring first to FIGS. 1 and 2 which illustrate one preferred embodiment of the present invention, the mechanism of lancet 10 is housed within a clam shell casing comprising an upper casing half 14 and lower casing half 16 as viewed in FIG. 1. The casing halves are permanently secured together such as for example, by pins 18 in holes 20 in the periphery of the respective casing halves as shown in the fragmentary view in FIG. 1. Alternatively, they may be secured by adhesive or other known securing means. It will be understood that the casing is held vertically in the user's hand, between the thumb and middle finger, such that the top and bottom casing halves become the sides in use. In order to provide maximum gripping of the rather small lancet, the external surfaces of the casing halves are preferably provided with irregular, high friction projections such, for example, raised circular surfaces 22 and/or a raised waffle pattern 24. Alternatively, it will be understood that other forms of high friction surfaces may be used.

The casing 12 is further provided with a slot 26 in the circumferential edge walls 28-29 of the two casing halves for the purpose of allowing the tip of a cutting blade 30 to project out of the casing so as to make the incision on the patient. Preferably, the wall surfaces 28-29 adjacent to slot 26 are bevelled at 32 above and below the slot in order to provide an improved ergometric shape which conforms to the incision area of the patient such as, for example, the heel area of an infant.

As further shown in FIGS. 1 and 2, one preferred embodiment of the lancet 10 includes a trigger button 34 including side walls 19 which slide downwardly in shallow grooves 21 on the outside surfaces of the casing halves. Trigger button 34 actuates the cutting mechanism, including blade 30 which is mounted in a holder 54, as will be more fully explained hereafter. In this regard, it will be understood that the upper surface 33 of the trigger button is engaged by the user's index finger to push the button downwardly such that, preferably, the upper portion of the button is provided with a high friction surface such as, for example, a plurality of ridges and grooves 33 which may be molded into the button. Alternatively, of course, other forms of high friction surfaces may be used to prevent the user's index finger from slipping when depressing the trigger button.

Figure 3A:
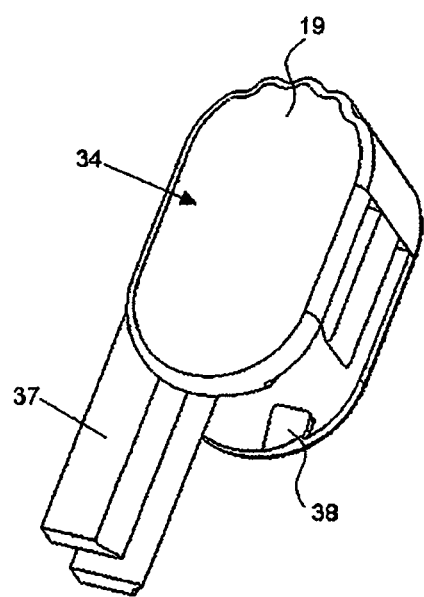
FIG. 3*a* is a perspective view of a trigger button.
Figure 3B:
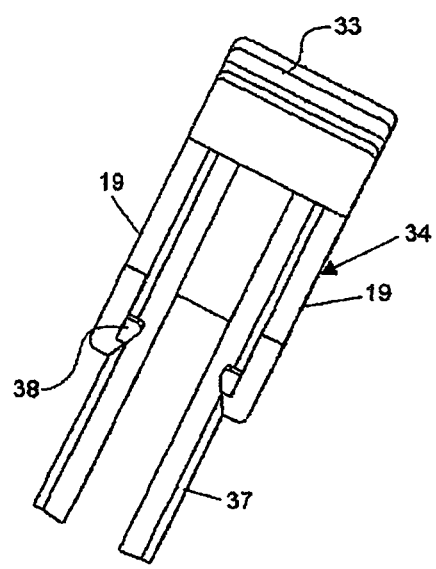
FIG. 3*b* is an elevational view of the trigger button.

As most clearly shown in FIGS. 3a and 3b, in one preferred embodiment the trigger button includes a pair of legs 37 which slide downwardly along grooves 36 in the inner surface of the casing. The bottom portions of the button include two enlarged tip portions 38 which slide in grooves 39 in the outside of the casing. The top portion of groove 39 is closed such that the enlarged tip portions become trapped in groove 39. Accordingly, once the button is inserted in the casing during manufacture of the lance, it is prevented from separating from the casing while being capable of vertical sliding movement.

As further shown in FIG. 2, in order to prevent accidental depression of the trigger button, a positive safety lock 40 is provided. In the first embodiment as illustrated in FIGS. 1-10, the safety lock is in the form of a manually removable lock 40 having a handle portion 41 the lower end of which is pressed against circumferential edge walls 28-29 and the upper end against button 34. The lock further includes one or more locking pins 42 which are received in one or more holes in button 34. In this manner, trigger button 34 cannot be accidentally depressed, but rather, can only be depressed after the user has pulled lock 40 out of locking engagement with both the casing and the trigger button.

Figure 4:
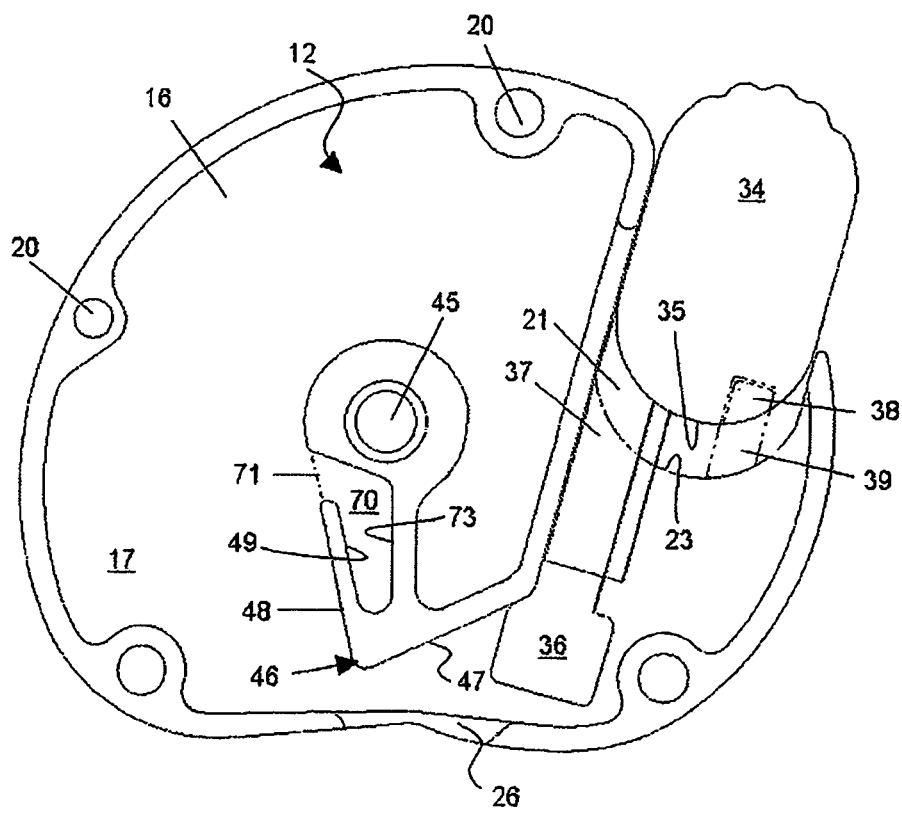
FIG. 4 is a top plan view of the bottom inner wall of the casing before the cutting mechanism is installed.
Figure 5:
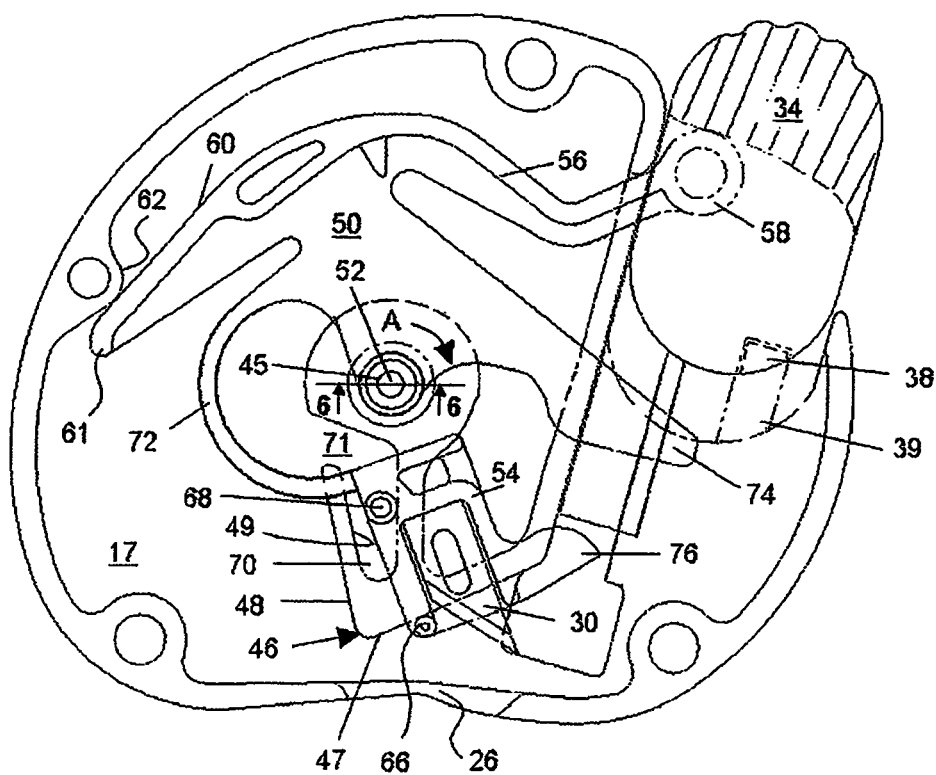
FIG. 5 is a top plan view, partly in cross-section, illustrating the cutting mechanism in a first pre-cutting position.
Figure 6:
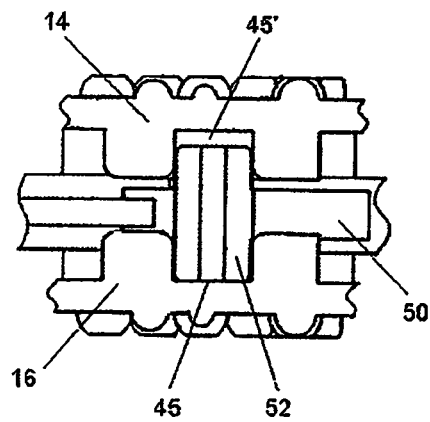
FIG. 6 is a cross-sectional view taken along view line 6-6.

Referring to FIG. 4, the lower casing half 16 is shown as it appears before the installation of the cutting mechanism. Lower casing half 16 includes a V-shaped cam 46 having a leading cam surface 47 and a trailing cam surface 48. Cam 46 also includes a V-shaped slot 70, and a second set of cam surfaces 49 and 73. While the detailed cam action will be more fully explained hereafter, it will be understood from FIG. 5, for example, that cam surfaces 47 and 48 are engaged by a first cam follower pin 66 mounted on blade holder 54, and cam surfaces 49 and 73 are engaged by a second cam follower pin 68 also mounted on blade holder 54. While cam 46 may be manufactured as a separate element and secured to casing half 16, it is preferred that the cam be molded on the inner surface 17 of casing half 16 as a one-piece, raised surface portion of casing half 16. As such, cam 46 also serves as a thickened portion of the casing half 16 and includes a centrally located hole or journal 45, as most clearly shown in FIGS. 4-6, for receiving a stub shaft 52 to be further described hereafter. Of course, while the cam portion and the journal portion are illustrated as being integral, it will be apparent that they may be molded or secured as two separate pieces. It is also to be understood that as shown in FIG. 6, upper casing half 14 includes an identical, mirror image cam with a journal 45' such that, when the casing halves are assembled, stub shaft 52 is secured at both ends in the journals.

The interior cutting mechanism will now be further described with reference to FIGS. 5-10. In one preferred embodiment, the cutting mechanism comprises the previously described blade 30 which is secured by known means in a blade holder 54. Blade holder 54 is connected by a relatively thin C-shaped spring element 72 to a pivoted hub plate 50 which includes the previously described stub shaft 52 which is preferably molded as an integral, one-piece element. Thus, hub plate 50 pivots in the direction of arrow A as shaft 52 pivots in journal 45. Hub plate 50 further includes an integral, one-piece trigger arm 56 having a smooth or rounded end 58 which is received between the spaced-apart legs 37 of trigger button 34. Accordingly, depression of the button causes plate 50 to pivot in the direction of arrow A about journal 45. Hub plate 50 further includes a second arm 60, hereinafter referred to as a "trip arm", and in the pre-cutting position illustrated in FIG. 5, the tip 61 of the arm bears against a protruding stop portion 62 of the casing. By reason of the cross-sectional area and composition of the one-piece plate 50, such as molded plastic, trip arm 60 has a predetermined amount of flexibility. Thus, when trigger button 34 is depressed, tip 61 snaps over stop portion 62 and the entire one-piece hub plate 50, including arms 56, 60 and blade holder 54, pivots extremely rapidly in the direction of arrow A from the pre-cutting position shown in FIG. 5 to the post-cutting position shown in FIG. 10. It will be understood that this entire motion from pre-cut to post-cut occurs virtually instantaneously; however, this motion will be described in the following distinct phases of motion.

Figure 7:
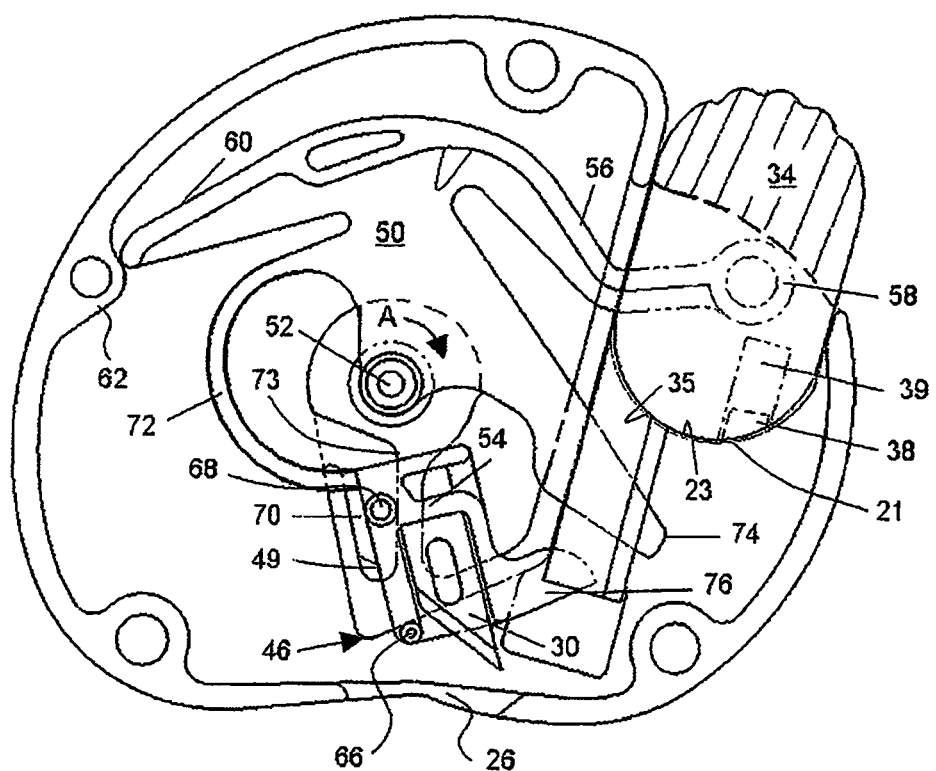
FIG. 7 is a top plan view, partly in cross-section, illustrating the cutting mechanism in a second pre-cutting position.

First, after the manual depression of button 34 to the position shown in FIG. 7, further downward motion of the button is stopped either because the bottom portion 35 of the button hits the top edge 23 of groove 21 in the casing, or in an alternative embodiment, the bottom of legs 37 hit the closed end of groove 36. In either event, the movement of the button stops, and therefore, the further pivoted movements of hub plate 50 and blade 30 are due to momentum of the parts and are independent of the user's strength or dexterity. This is due to the substantial force built up in flexible finger 60 before it snaps over abutment 62, which then imparts a very high arcuate velocity and momentum to the entire one-piece hub plate and the blade.

Figure 8:
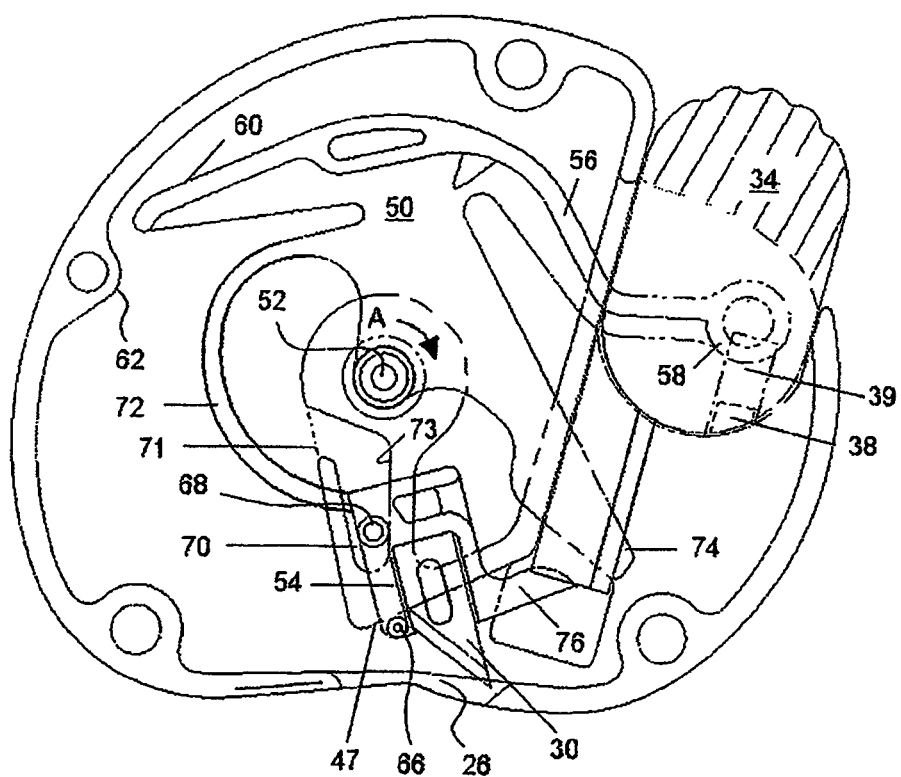
FIG. 8 is a top plan view, partly in cross-section, illustrating the cutting mechanism in a third pre-cutting position.

As further shown in FIG. 8, hub plate 50 continues to pivot about shaft 52 while C-shaped tension spring 72 maintains cam follower 66 on blade holder 54 in engagement with leading cam edge 47. Because of the V-shape of the cam, the blade is forced downwardly toward slot 26, while cam follower 68 slides along cam surface 73. This motion continues as the hub plate continues to pivot, thereby drawing arm 56 and end 58 downwardly between spaced legs 37 of button 34 as blade 30 approaches the right-hand edge of slot 26 as viewed in FIG. 8.

Figure 9:
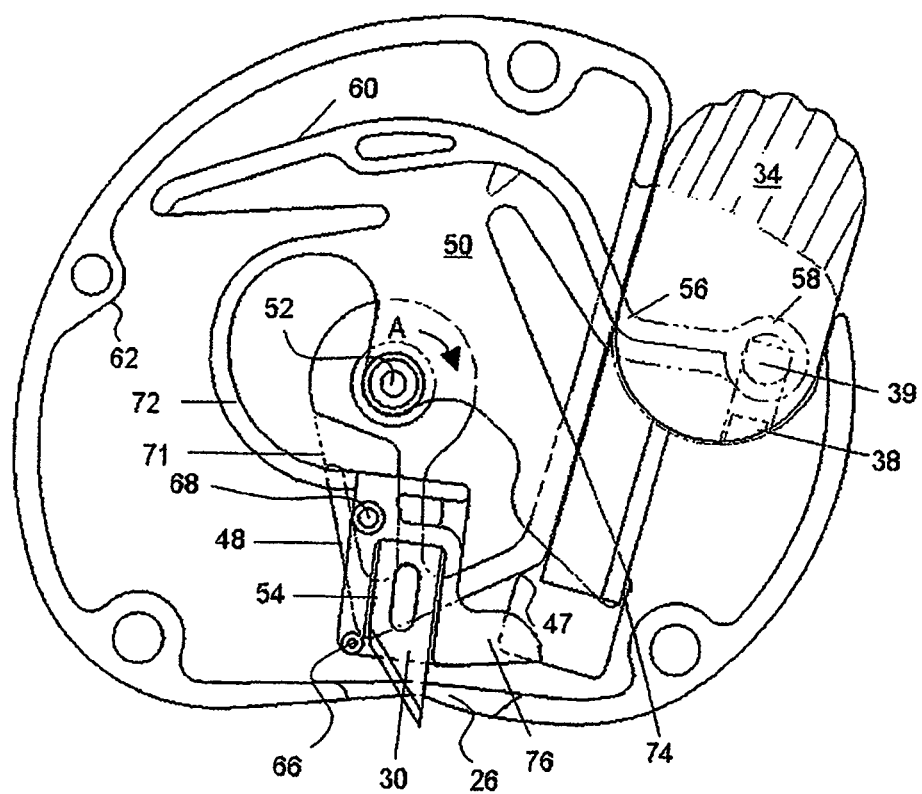
FIG. 9 is a top plan view, partly in cross-section, illustrating the cutting mechanism in approximately the mid-point of the incision.

FIG. 9 shows the incision at its point of deepest penetration into the patient. At this point, cam follower 66 is at the end of leading cam surface 47 and is about to move upwardly along trailing cam surface 48. It will also be noted that cam follower 68 is also about to begin moving upwardly in engagement with cam surface 49 in slot 70 due to the tension of spring 72 pulling the blade holder upwardly. In addition, it should be noted that hub plate 50 is illustrated as having an additional arm 74, and a projection 76 extending from blade holder 54 toward arm 74. Thus, if desired in an alternative embodiment, the shape and angle of arm 74, and the length of projection 76, may be designed such that arm 74 may be made to engage projection 76 and thereby add a pushing force on the blade holder during the cutting phase. However, it has been found that such an additional force is not necessary, over and above the substantial momentum of the entire cutting mechanism as previously described, such that arm 74 and projection 76 may be entirely eliminated thereby adding to the cost reduction of the mechanism.

Figure 10:
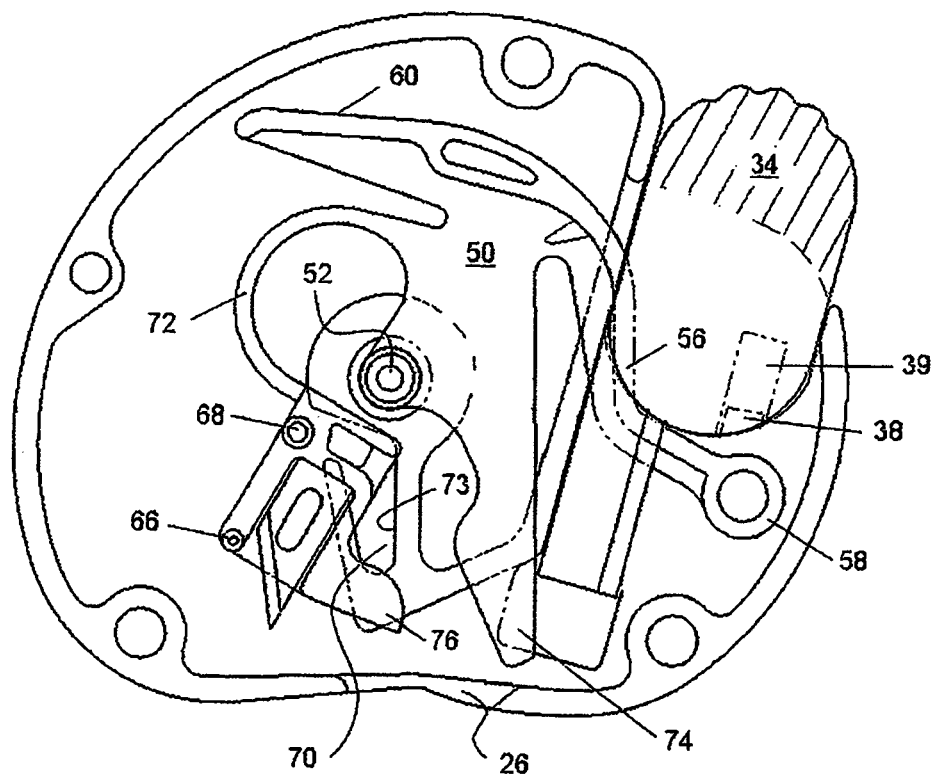
FIG. 10 is a plan view, partly in cross-section, illustrating the cutting mechanism in the post-cutting position.

FIG. 10 illustrates the final, post-cutting position in which the blade has completed the incision, and it has been retracted entirely into the interior of the casing such that it is not a hazard to any nearby personnel. This movement of the blade and holder is made possible by the provision of opening 71 at the upper end of cam 48 through which cam follower 68 passes outwardly from slot 70 under the action of spring 72 which flexes into its predetermined non-tensioned shape.

Figure 11:
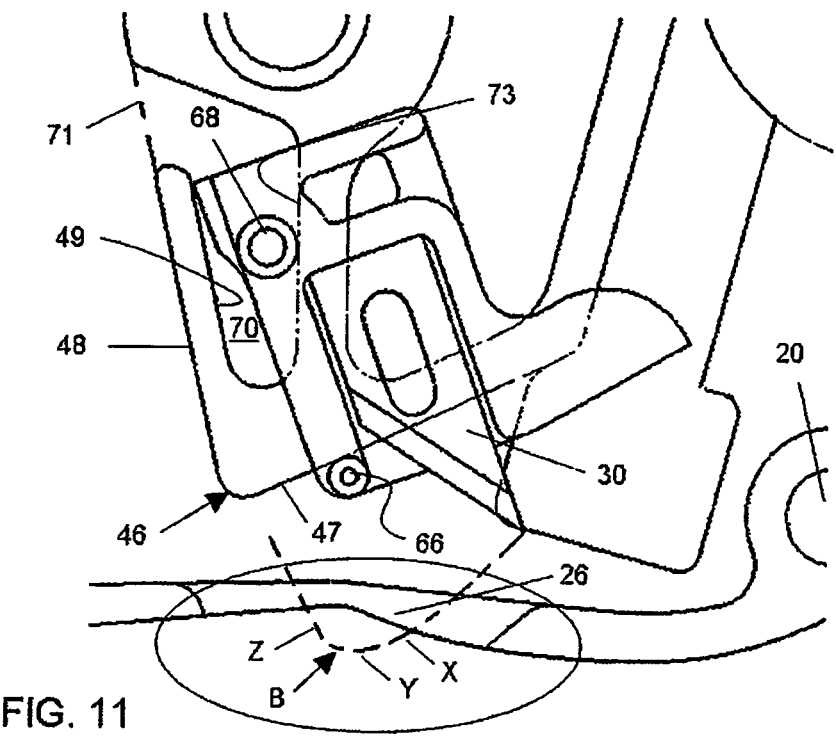
FIG. 11 illustrates the off-center parabolic shape of the cutting path of the blade.

As further illustrated in the dotted-line FIG. 11, dotted line B illustrates the cutting path of the tip of blade 30 as it performs the incision, and it will be noted that the cutting path of the blade is entirely a smooth curve with no jagged portions. It will be further noted that the initial portion X of the cutting path is at a relatively sharp, acute angle of less than 45 degrees with respect to slot 26 against which the patient's skin is in contact. This produces a clean and sharp initial incision which then becomes wider until it is subsequently withdrawn cleanly at portion Z, which is also at an acute angle but less acute than that of portion X. This precisely defined path, hereinafter referred to as an "off-center parabola", in combination with the high speed motion and momentum of the blade produced by the stored energy of arm 60 before it snaps over abutment 62, has been discovered to produce a substantially improved incision which produces the required amount of blood sample in a substantially less painful manner. Also, the speed and accuracy of the cutting is absolutely the same regardless of the dexterity or strength of the finger motion of the user. Thus, unlike the prior art which often produces a relatively jagged cut due to the jerking motion of driving springs, and or the uneven pressure by the finger of the user, the lancet of the present invention produces a clean, smooth and non-jagged incision of an ideal shape for obtaining blood samples with less pain inflicted on the patient, who usually is an infant. In addition, the fact that all of the moving parts and elements of the cutting mechanism comprise a single, one-piece element allows the entire mechanism to be mass produced by molding only the one-piece hub plate 50 at a substantially lower cost than previously possible.

Figure 12:
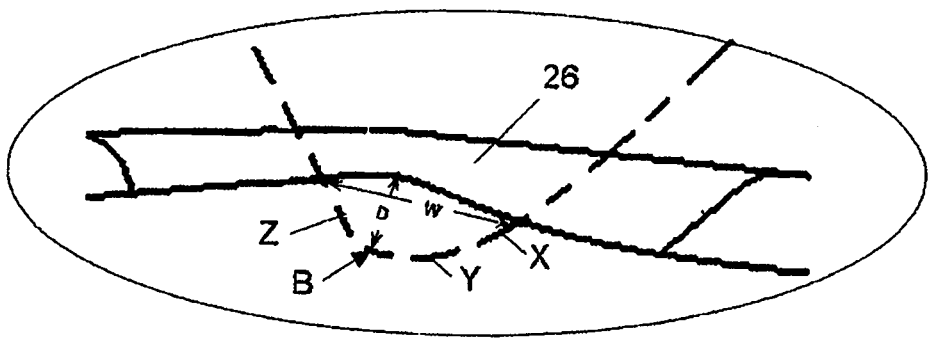
FIG. 12 is an enlarged view of the cutting path shown in FIG. 11.

As further shown in FIG. 12, the cutting path of the tip of the blade, and hence the profile of the resulting incision, comprises a first path portion X which has a component of motion in the direction of the width W of the incision as the blade tip enters the skin and penetrates to depth D. Thereafter, the tip executes a smooth reversing curve at B, and then the blade is extracted along path Z which has a lesser component of motion along the width, and a larger component of motion along the direction of the depth of the cut which withdraws the blade with minimum width of cut. As a result of this precisely defined, and repeatable incision profile, both the depth and width of the cut is minimized and yet able to produce a completely sufficient blood sample.

Figure 13:
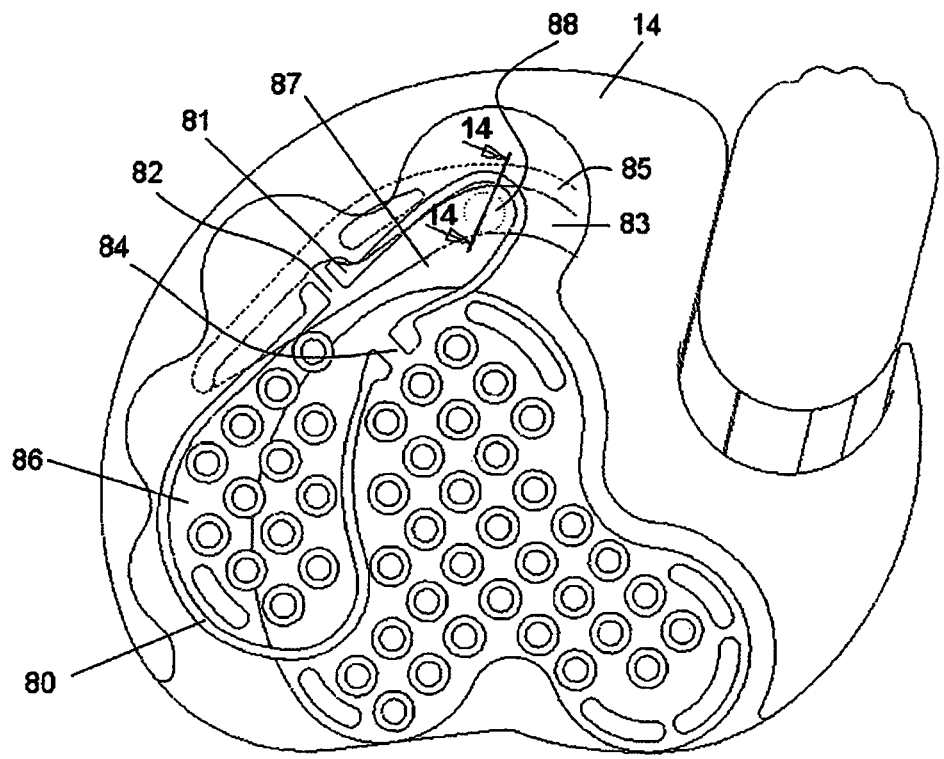
FIG. 13 is a top plan view of a second embodiment of the lance.
Figure 14:
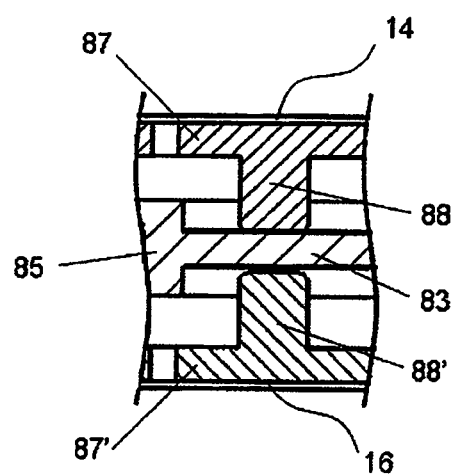
FIG. 14 is a cross-sectional view taken along view line 14-14 of FIG. 13.
Figure 15:
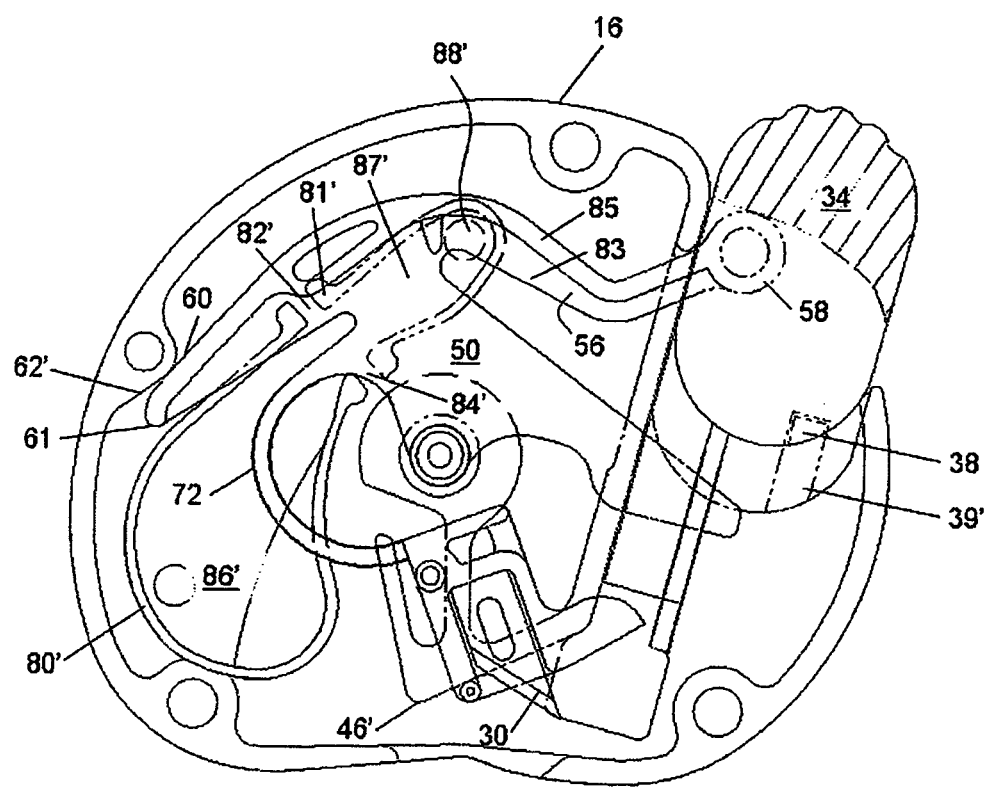
FIG. 15 is a top plan view of the second embodiment with the top cover removed.

A second preferred embodiment of the present invention will now be described with reference to FIGS. 13-15. The cutting mechanism of this embodiment is the same as that previously described, and accordingly the same reference numerals are applied to FIGS. 13-15 as in FIGS. 1-12. The difference of the second embodiment from the first embodiment pertains to the positive safety lock. In this embodiment, as shown most clearly in FIGS. 13 and 15, each of the upper and lower casing halves 14 and 16 are cut out with arcuate slots 80,80' and 81,81' to form two pivoted levers one on each side of the casing. Each of the two pivoted levers has a relatively large portion 86,86' and a smaller portion 87,87'. Between the slots the casing is uncut so as to form connecting portions 82,82' and 84,84' which function as pivots allowing tilting movement of the large portions of the lever relative to the smaller portions. That is, when the user depresses portions 86,86' into the lancet with his thumb and middle finger, the smaller portions 87,87' are moved outwardly away from the casing. As shown most clearly in FIG. 14, locking pins 88,88' are connected to and carried by the smaller pivoted lever portions 87,87'. When the levers are not depressed, the locking pins 88-88' extend into the cutting mechanism and engage one of the arms on hub plate 50 such as, for example, between arms 56 and 60. In this regard it will be understood that, in one preferred embodiment, arms 56 and 60 comprise a thinner portion 83 and a thicker edge portion 85 as shown in FIGS. 14 and 15. Thus, the locking pins engage the edges of the thicker portion 85 when lever portions 86,86' are not depressed. This locking engagement prevents movement of arms 56 and 60 and thereby locks hub plate 50 in fixed, locked position. However, when the pivoted lever portions 86,86' are depressed by the user, portions 87,87' move outwardly of the casing and pull the locking pins out of engagement with arms 56,60 thereby releasing the hub plate for pivoted movement as previously described. In this manner, the second embodiment performs all of the functions and advantages previously described with respect to the first embodiment, and it will be apparent that other forms of pivoted locks may be used, such as for example, holes in any of the arms which may be engaged by pins, abutments or the like.

A further embodiment will now be described with reference to FIGS. 16-21. Since the majority of the elements of this embodiment are the same as those previously described, the same numerals have been applied to those elements which are the same. As shown in each of FIGS. 16-21, the first difference of this embodiment is that trigger button 34 is formed as an integral, one-piece portion of hub plate 50, preferably as a single molded part, and connected to the hub plate by an intermediate connecting portion 89 of plate 50.

Figure 16:
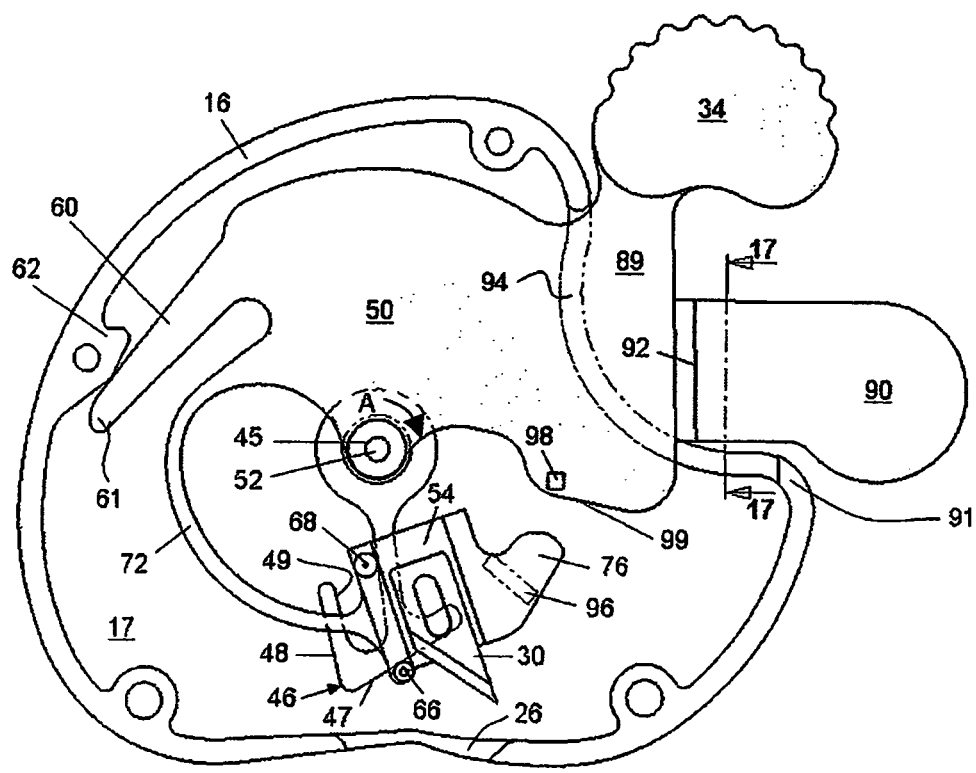
FIG. 16 is a top plan view of a third embodiment of the cutting mechanism in a first pre-cutting position.
Figure 17:
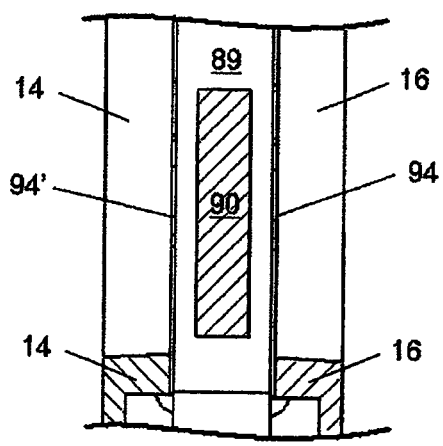
FIG. 17 is a cross-sectional view along view line 17-17 of FIG. 16.
Figure 18:
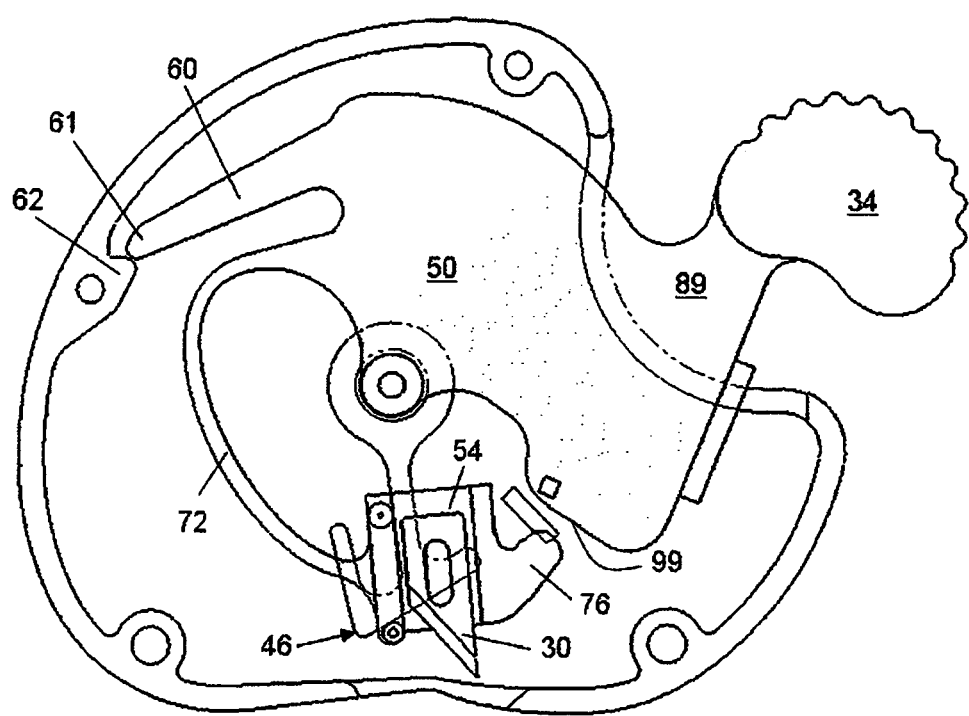
FIG. 18 is a top plan view of the third embodiment showing the cutting mechanism in a second pre-cutting position.
Figure 19:
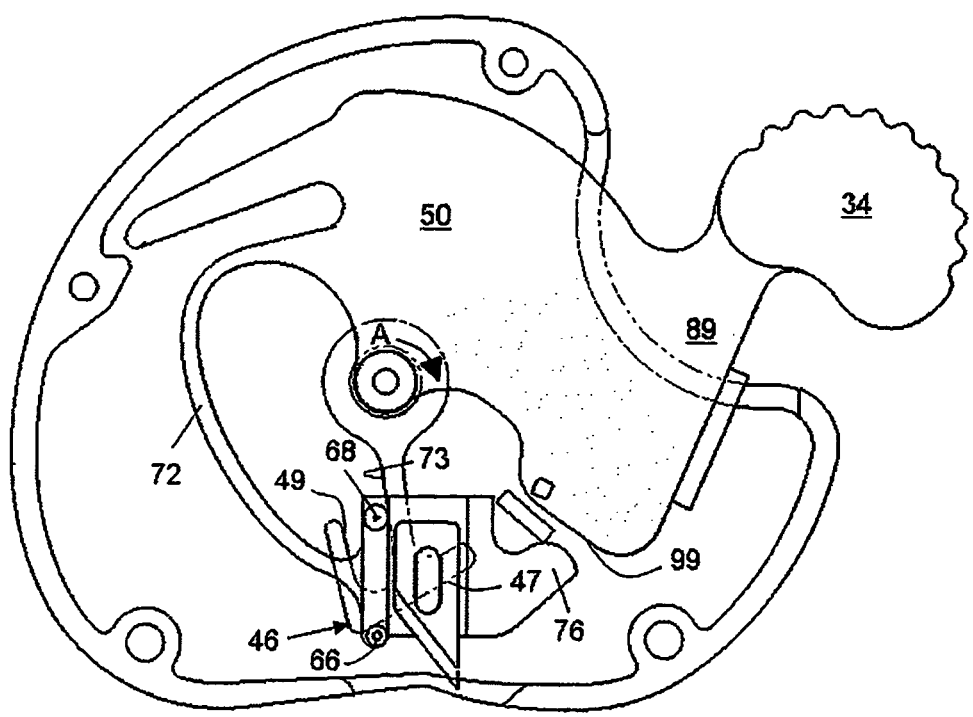
FIG. 19 is a top plan view of the third embodiment showing the cutting mechanism in a third pre-cutting position.
Figure 20:
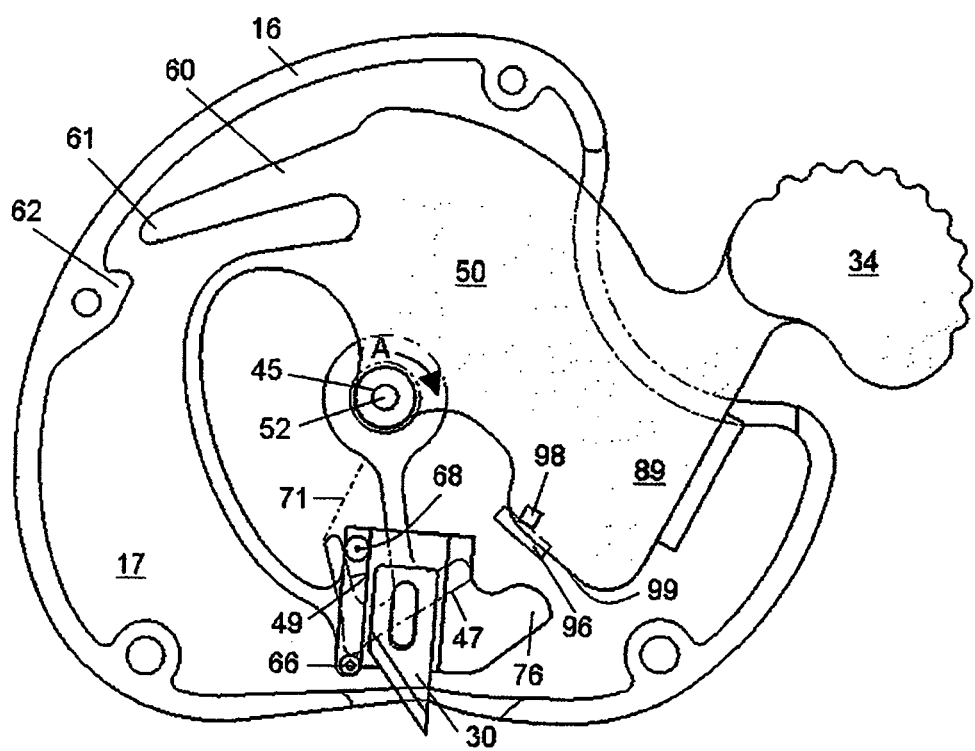
FIG. 20 is a top plan view of the third embodiment showing the cutting mechanism in the cutting position.

A second difference from the embodiments previously described is the provision of a locking tab 90 which is also preferably an integral, one-piece portion of hub plate 50 As most clearly shown in FIGS. 16 and 17, locking tab 90 extends through a slot 94 formed between the casing halves. Thus, any accidental pushing down of the button is prevented by the bottom edge of the tab striking the casing at the bottom end 91 of the slot. However, tab 90 also includes a groove or other weakened portion 92 whereby the locking tab may be broken off by the user immediately prior to using the lancet to make an incision. Accordingly, when the user breaks off tab 90, connecting portion 89 of the plate is free to move downwardly through slot 94 and thereby pivot hub plate 50 in the direction of arrow A.

Figure 21:
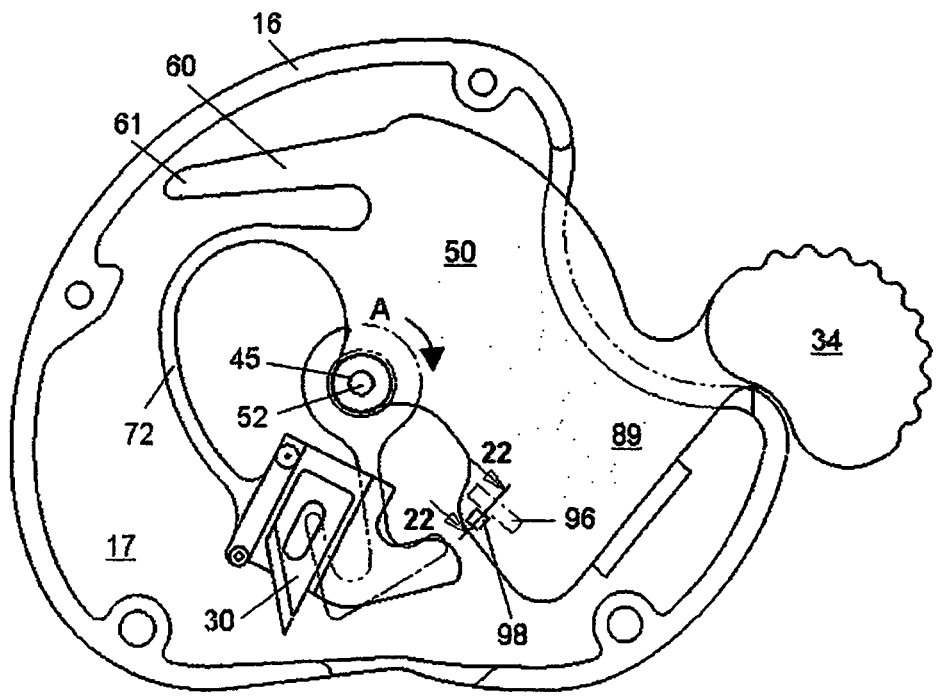
FIG. 21 is a top plan view of the third embodiment showing the cutting mechanism in the post-cutting position.
Figure 22:
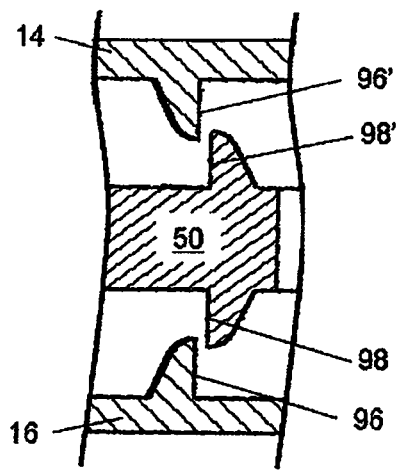
FIG. 22 is a cross-sectional view taken along view line 22-22 of FIG. 21.
Figure 23:
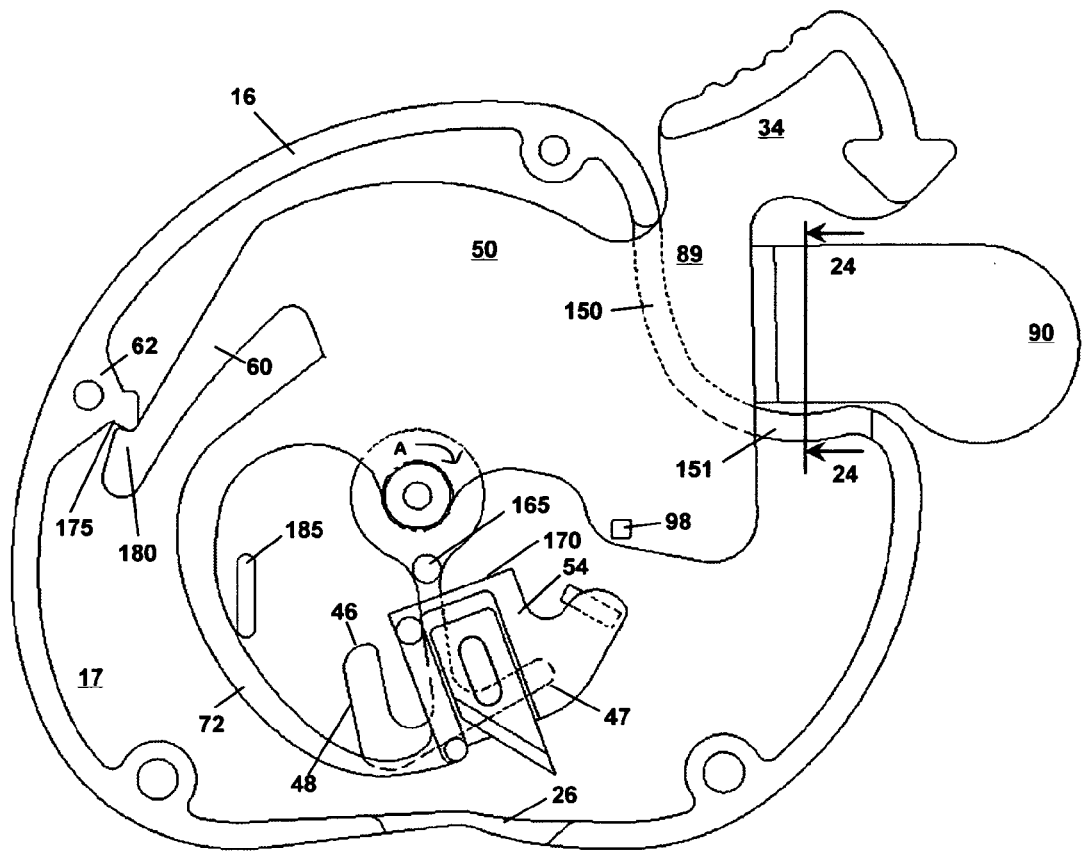
FIG. 23 is a top plan view of the fourth embodiment showing the cutting mechanism in a first pre-cutting position.

The third difference of this embodiment from those previously described is the provision of a post-cut lock as most clearly shown in FIGS. 21 and 22 whereby the blade, which is retracted into the casing after making the incision, is positively locked in the post-cut position. In the preferred embodiment, this post-cut lock comprises a pair of projections 96, 96' which are molded into or otherwise secured to the inner surfaces of each of the casing halves. Projections 96, 96' are preferably provided with smooth and slightly angled upper surfaces which are engaged by the bottom surfaces of a pair of detents 98, 98' carried by hub plate 50. Thus, as shown most clearly in FIG. 22, when the hub plate has almost completed its full pivoted movement, and the blade has been retracted into a safe position in the casing as shown in FIG. 21, the last movement of the plate causes detents 98, 98' to be forced downwardly between and below projections 96, 96' which spread slightly due to the slight flexibility of the casing walls. Thus, the hub plate is prevented by projections 96, 96' from moving in the opposite direction. Accordingly, the hub plate 50, blade holder 54 and blade 30 are positively locked in a safe retracted position so as not to be able to injure any nearby personnel.

The preferred mode of operation of this embodiment is as follows. First, the user breaks off locking tab 90 whereby hub plate 50 is free to be pivoted by the user pushing trigger button downwardly with the user's index finger. However, at this time finger 61 is in engagement with abutment 62, and its length and degree of resilience is such that a certain degree of force is required to push the button downwardly. As the user increases this force by further pressure on the button, finally finger 61 snaps over abutment 62 whereby plate 50 is pivoted extremely rapidly in the direction of arrow A. Such high velocity of the hub plate creates sufficient momentum to carry the plate and blade completely through the cutting and post-cutting positions illustrated in FIGS. 18-21 under the action of spring 72 and the cam surfaces on cam 46 as previously described in the prior embodiments. Therefore, in this mode, the entire force required is provided by momentum, and the user's finger merely follows the motion of the button rather than pushing the button to its final position.

Alternatively, the lancet of this embodiment may be operated in a manual mode in which the user's finger continues to push the button throughout its path from the FIG. 16 to FIG. 21 positions, thereby assisting the force of a lesser amount of momentum such as may result from the use of a shorter and/or more flexible finger 61 which produces less velocity, and hence, less momentum.

As another alternative mode, the lancet of this embodiment may operate in a mode in which the design of finger 61 is such as to create sufficient momentum to accomplish the required cutting phase without manual assistance, but additional manual force is applied to the button after the incision is completed. That is, the only additional manual force is to assist in the final phase to force detents 98 to pass through projections 96 to post-lock the blade in the casing. In another alternative embodiment, it will be noted that blade holder 54 is illustrated as including a projection 76 as in the first embodiment. Thus, the size and shape of projection 76 and that of portion 99 of hub 50 may be designed so that portion 99 strikes projection 76 and thereby assists the force of the momentum to make the incision. However, as in the first embodiment, projection 76 maybe eliminated and the lancet may be operated in either one of the above two describe modes. Thus, it is to be understood that the specific design of finger 61 may be used in each of the described embodiments to generate the specific amount of momentum which is desired for a particular configuration of that embodiment.

Yet another embodiment will now be described with reference to FIGS. 23-27. Since the majority of the elements of this embodiment are the same as those in the previous embodiment, only the numerals relevant to the description below have been applied to the elements in FIGS. 23-27. The differences from the previous embodiment have been explained in detail below.

As shown in each of FIGS. 23-27, the first difference of this embodiment is that the trigger button 34 is shaped ergonomically. The shape of the trigger button is such that it matches with the shape of the thumb of the user. This shape produces less strain on the user's finger.

Figure 24:
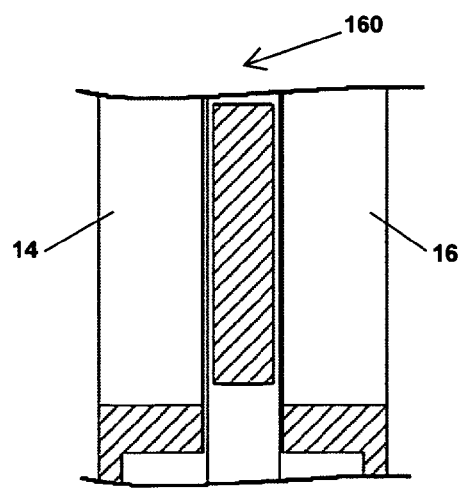
FIG. 24 is a cross-sectional view along view line 24-24 of FIG. 23.

A second difference is that the profile 150 of the lower casing half 16 and the upper casing half 14 adjacent the trigger button 34 have been modified to reduce the travel distance of the trigger button. It is apparent from FIGS. 23-27 that the portion 151 of the profile has been curved upwards to result in a shorter travel distance of the trigger arm. The upper casing half 14 and the lower casing half 16 together comprise the housing 160 as illustrated in FIG. 24.

A third difference is the provision of a reinforcing structure 165, such as a pin or a small projection in the housing and located adjacent the centre of the housing 160 to resist any inward deflection of one of the main walls of the upper casing half towards the lower casing half or one of the main walls of the lower casing half towards the upper casing half. The reinforcing structure 165 is preferably located on the cam 46. In other words, the purpose of the pin is to maintain a gap between the upper and lower casing half and prevent them from pinching on the blade holder 54 when the cutting device is gripped by the user. When the blade holder is pinched, it is prevented from moving and the cutting device can no longer be used.

A fourth difference is the provision of a ridge 170 on the blade holder 54 to provide a continuous flat surface, so that there will be no corners which can jam the movement of the blade holder hub if they are accidentally blocked from the sides of the cam 46 from moving.

A fifth difference is that the leading cam surface 47 is longer when compared with the previous embodiment. By having a longer leading cam surface in the V-cam profile, there will be an increase in the length of the cut.

Figure 25:
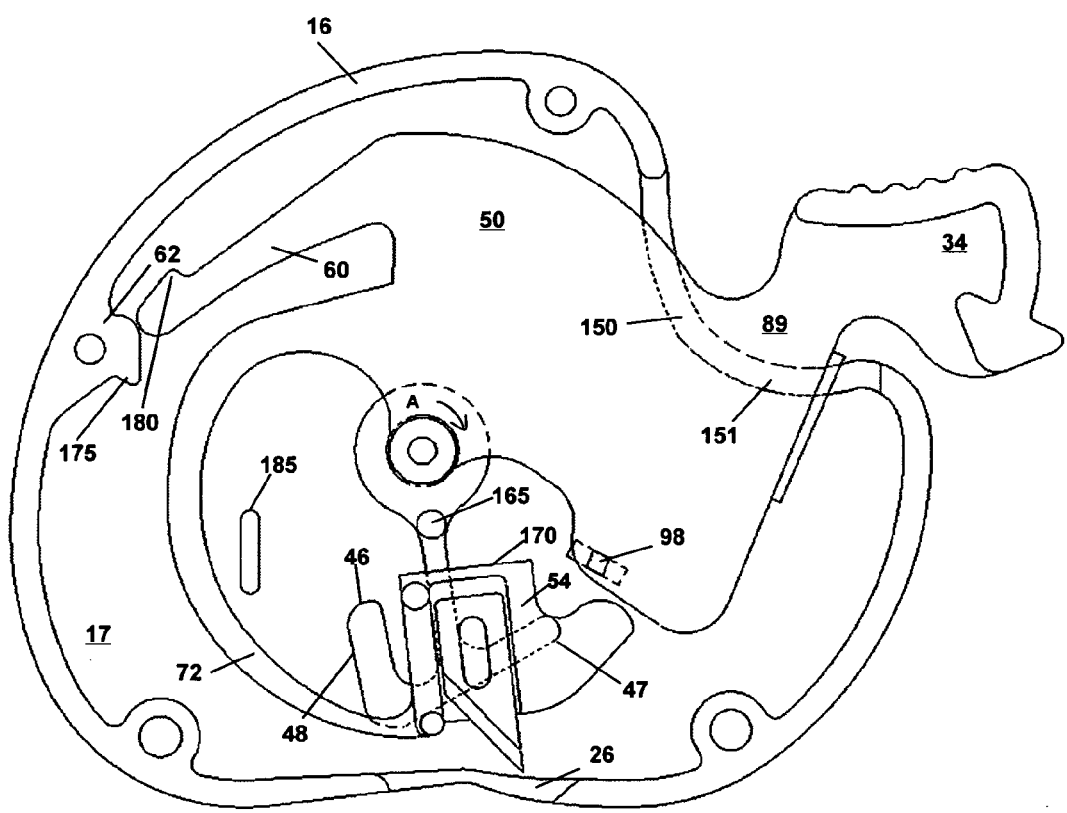
FIG. 25 is a top plan view of the fourth embodiment showing the cutting mechanism in a second pre-cutting position.
Figure 26:
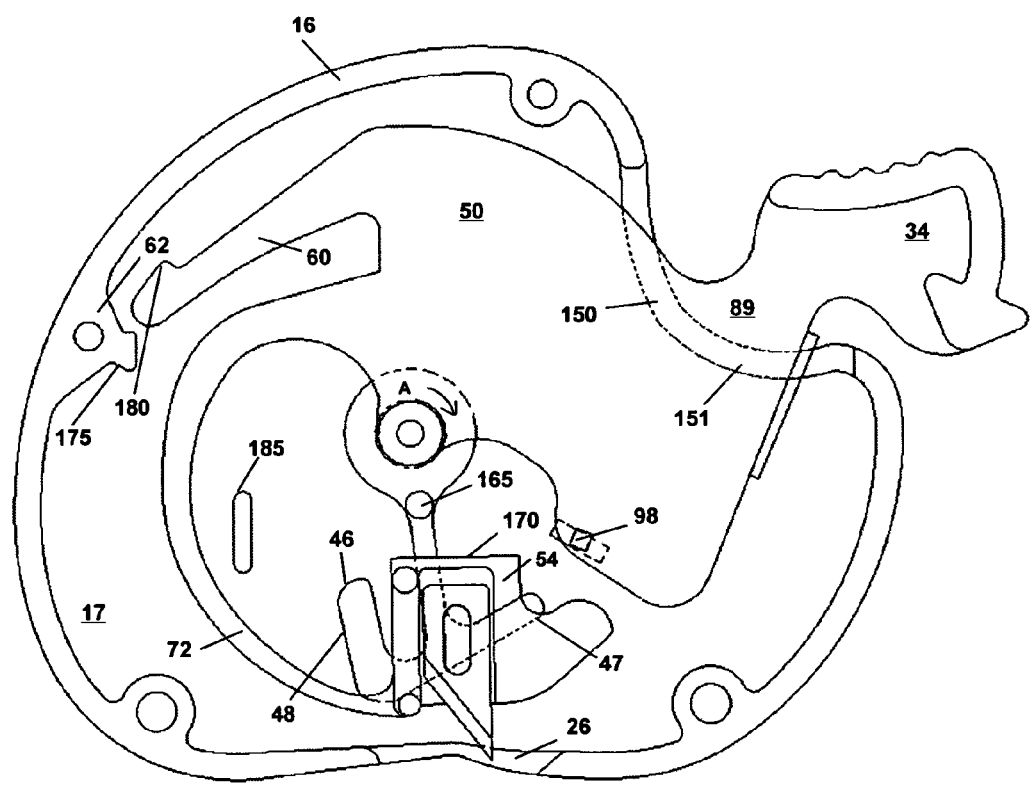
FIG. 26 is a top plan view of the fourth embodiment showing the cutting mechanism in a third pre-cutting position.
Figure 27:
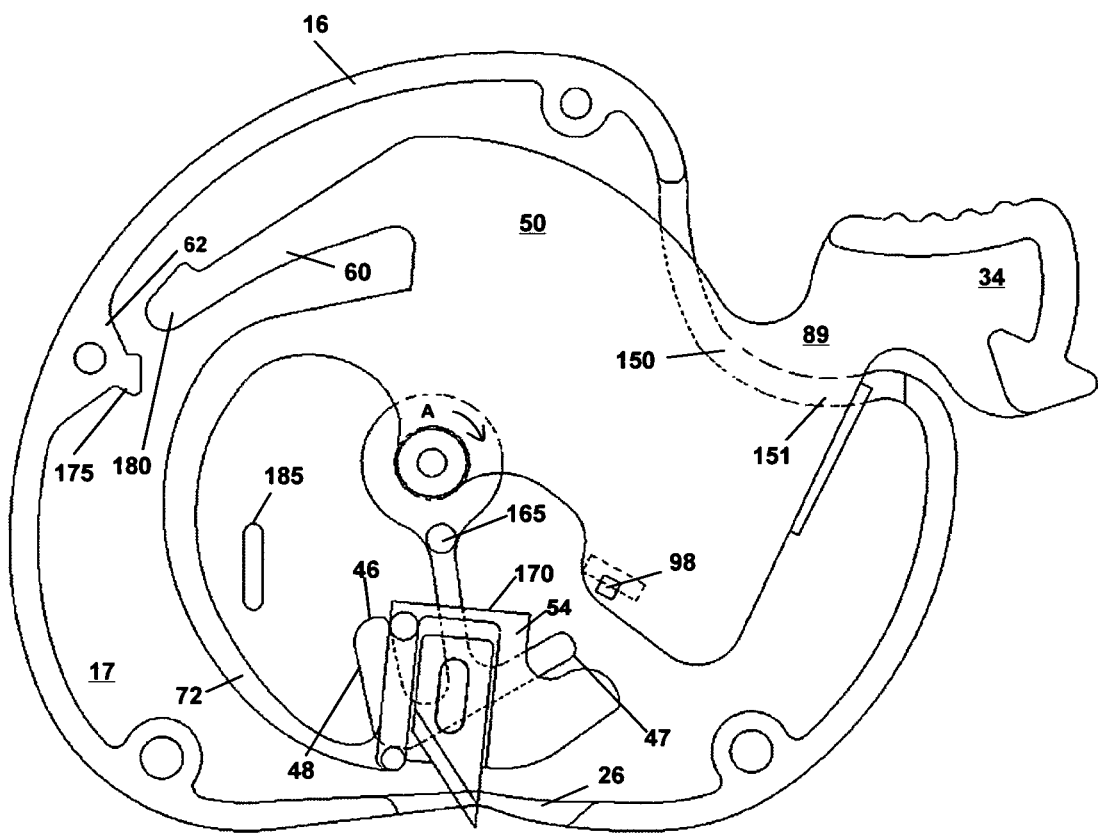
FIG. 27 is a top plan view of the fourth embodiment showing the cutting mechanism in the cutting position.
Figure 28:
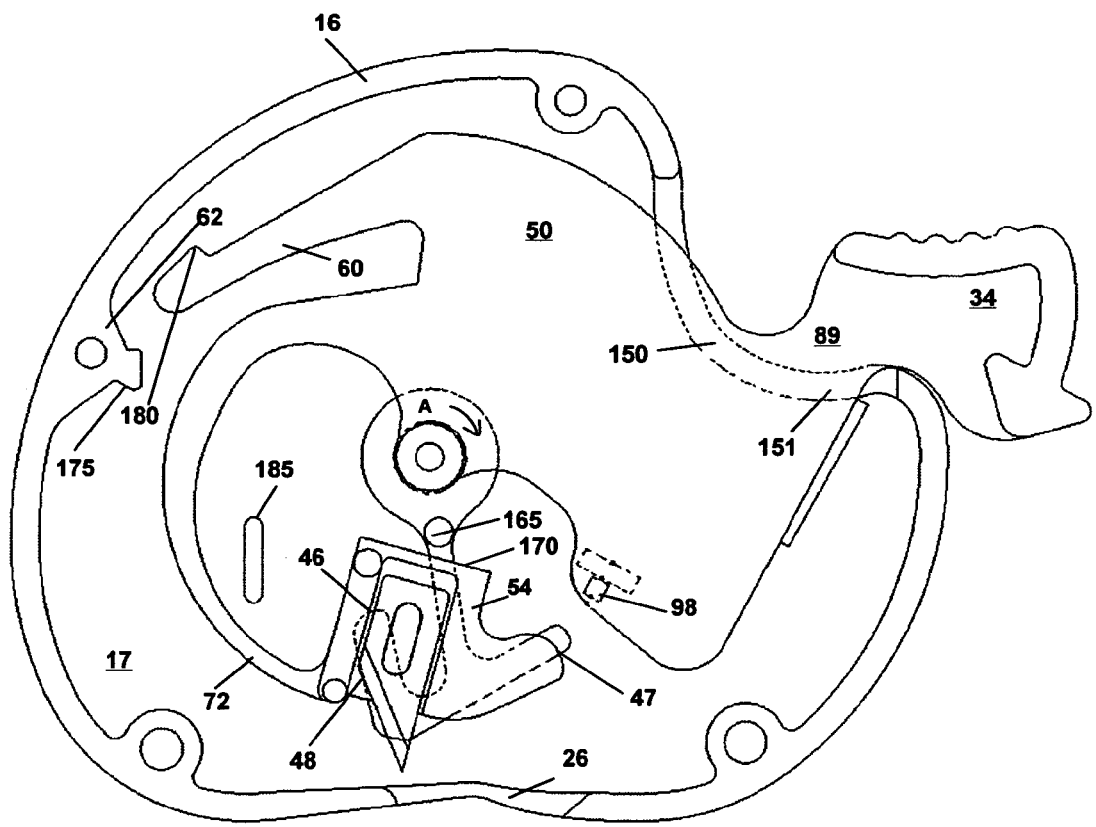
FIG. 28 is a top plan view of the fourth embodiment showing the cutting mechanism in the post-cutting position.

The next difference is in the shape and arrangement of the abutment 62 in the lower casing half 16 of the housing 160 and the arm 60. There is provided a first stop 175 on the tip of the abutment 62 and a corresponding catch 180 on the arm 60. The arm is a resilient arm and the catch engages against the first stop 175 in the pre-cutting position. When the trigger button is pressed by the user, the pivoted hub plate 50 pivots which causes the deflection of the arm 60 to a deflected position for the catch to be released from the first stop. The position of the pivoted element 50 and the arm 60 after deflection is illustrated in FIG. 25. Once deflected, the pivoted element is free to pivot and moves quickly with the cutting blade moving through the cutting position. The presence of the catch and the first stop prevents any slight movement of the cutting blade, before the catch 180 is fully released from the first stop 175. This prevents any pre-mature exposure of the cutting blade. In other words, pre-mature in this context is the cutting blade being exposed out of the slot 26 in the housing, even before the cutting blade moves through the cutting position at full speed.

The last difference is the presence of a second stop 185 in the lower casing half 16 of the housing 160. In the event of the blade holder being jammed and prevented from moving during the pivoting action of the pivoted element, stress builds up in the flexible spring element 72 and it suffers permanent deformation and becomes elongated due to over flexing. Subsequently if the blade holder becomes free to move, the elongated spring element 72 pushes the cutting blade 54 out of the slot 26 and the cutting blade dangles freely, posing a hazard to the user. The second stop 185 positioned adjacent the spring element prevents the spring element from over flexing in the event of stress build up in the spring element.

It is to be understood that the foregoing description of several preferred embodiments is intended to be purely illustrative of the principles of the invention, rather than exhaustive thereof, and that changes and variations will be apparent to those skilled in the art, and that the present invention is not intended to be limited other than expressly set forth in the following claims.

The invention claimed is:

1. A cutting device comprising:
 a pivoted element including a trigger arm;
 a cutting blade;
 a flexible spring element connecting said blade to said pivoted element; and
 cam elements of a size and shape cooperating with said flexible spring element such as to move said blade from a pre-cutting position to and through a cutting position along a substantially parabolic path upon movement of said trigger arm; wherein the cutting device further includes a housing having a first stop; and the pivoted element further includes a second relatively flexible arm connecting the flexible spring element to the trigger arm, the second relatively flexible arm having an enlarged end comprising a catch, the catch comprising an inclined surface extending from the second relatively flexible arm, the inclined surface of the catch and the first stop configured to be in engagement to prevent movement of the blade in the pre-cutting position, the pivoted element being arranged to pivot within the housing responsive to activation of the trigger arm by a user of a force which causes the deflection of the second relatively flexible arm to a deflected position for the inclined surface of the catch to release from the first stop, thereby allowing the flexible spring element and the cutting blade to move through the cutting position assisted by action of the second relatively flexible arm reverting from the deflected position.

2. The cutting device of claim 1 wherein the cam elements include a V-shaped cam having a leading cam surface and a trailing cam surface, and at least one cam follower element connected to said blade for engaging said leading and trailing cam surfaces.

3. The cutting device of claim 1 wherein the cam elements include a V-shaped slot, and a cam follower element connected to said blade and engaged in said slot wherein said slot restrains said blade to move in the substantially parabolic path while said pivoted element pivots from the pre-cutting position to and through the cutting position of the blade.

4. A cutting device as claimed in claim 3, further comprising: a second stop in the housing being to restrict the flexible spring element from over flexing.

5. The cutting device of claim 1 further comprising a trigger element connected to said trigger arm whereby depression of said trigger element causes said pivoted element to pivot from the pre-cutting position of the blade toward the cutting position of the blade.

6. The cutting device of claim 1 further comprising a blade holder holding said blade, and a third arm connected to said pivoted element which pivots into engagement with said blade holder.

7. The cutting device of claim 1 further comprising a trigger element and a manually operated lock, said lock including at least one projection engaging said trigger element for preventing said pivoted element from moving out of a locked position until such time as said projection is removed from said trigger element.

8. The cutting device of claim 1 wherein said pivoted element and said trigger arm and said flexible arm form a single, molded part.

9. The cutting device of claim 1 further comprising a manually operated lock, said lock including at least one pivoted lever, and wherein said pivoted lever includes a locking pin preventing movement of said cutting blade until said pivoted lever is pivoted by a user.

10. The cutting device of claim 9 further comprising a second pivoted lever including a second locking pin.

11. A cutting device as claimed in claim 1, further comprising: a reinforcing structure in the housing for resisting inward deflection of a main wall of one of an upper casing half and a lower casing half towards the other of the upper casing half and the lower casing half.

12. The cutting device of claim 1 wherein the cam elements include a V-shaped cam having a leading cam surface and a trailing cam surface, and two cam follower elements connected to said blade for engaging said leading and trailing cam surfaces.

13. A lancet comprising:
a cutting blade for making an incision on a patient;
mechanical means for moving said cutting blade from a pre-cutting position through an extended cutting position to a retracted position along an incision path comprising an off-center parabolic path, the mechanical means including a pivoted element and a trigger arm;
a blade slot: wherein the incision path includes a first path portion extending at a first acute angle with respect to said blade slot, and a second path portion extending at a second acute angle greater than the first acute angle with respect to said blade slot;
a housing having a first stop;
the mechanical means further includes a second relatively flexible arm connecting the pivoted element to the trigger arm, the second relatively flexible arm having an enlarged end comprising a catch, the catch comprising an inclined surface extending from the second relatively flexible arm, the inclined surface of the catch and the first stop configured to be in engagement to prevent movement of the cutting blade in the pre-cutting position, the mechanical means being arranged to pivot within the housing responsive to activation of the mechanical means by a user of a force which causes the deflection of the second relatively flexible arm to a deflected position for the inclined surface of the catch to release from the first stop, thereby allowing the cutting blade to move through the cutting position assisted by action of the second relatively flexible arm reverting from the deflected position;
wherein the mass and velocity of said pivoted element is sufficient to move said blade from the pre-cutting position partially through the incision path toward the retracted position, and said trigger arm completes the movement of said blade.

14. A cutting device comprising;
a pivoted element including a trigger arm;
a cutting blade;
a flexible spring element connecting said blade to said pivoted element;
cam elements of a size and shape cooperating with said flexible spring element such as to move said blade from a pre-cutting position to and through a cutting position along a substantially parabolic path upon movement of said trigger arm; and
a frangible locking element connected to and carried by said pivoted element to prevent pivoted movement of said pivoted element prior to breaking off said locking element;
the cutting device further includes a housing having a first stop; and
the pivoted element further includes a second relatively flexible arm connecting the flexible spring element to the trigger arm, the second relatively flexible arm having an enlarged end comprising a catch, the catch comprising an inclined surface extending from the second relatively flexible arm, the inclined surface of the catch and the first stop configured to be in engagement to prevent movement of the blade in the pre-cutting position, the pivoted element being arranged to pivot within the housing responsive to activation of the trigger arm by a user of a force which causes the deflection of the second relatively flexible arm to a deflected position for the inclined surface of the catch to release from the first stop, thereby allowing the flexible spring element and cutting blade to move through the cutting position assisted by action of the second relatively flexible arm reverting from the deflected position.

15. The lancet of claim 14 further comprising a trigger button rigidly connected to said trigger arm.

16. The lancet of claim 15 wherein said pivoted element and said trigger arm and said button form a single, molded part.

17. The lancet of claim 14 further comprising a first locking means carried by said pivoted element and stationary mating locking means for locking the cutting blade in a retracted post-cutting position.

* * * * *